(12) United States Patent
Eastham et al.

(10) Patent No.: US 6,984,668 B1
(45) Date of Patent: Jan. 10, 2006

(54) METAL-COMPOUND CATALYZED PROCESSES

(75) Inventors: Graham Ronald Eastham, Durham (GB); Raymond Anthony Hadden, Durham (GB); David William Johnson, Thirsk (GB)

(73) Assignee: Lucite International UK Limited, Hampshire (GB)

( * ) Notice: Subject to any disclaimer, the term of this patent is extended or adjusted under 35 U.S.C. 154(b) by 0 days.

(21) Appl. No.: 10/048,595

(22) PCT Filed: Aug. 2, 2000

(86) PCT No.: PCT/GB00/02981

§ 371 (c)(1),
(2), (4) Date: Jun. 27, 2002

(87) PCT Pub. No.: WO01/10551

PCT Pub. Date: Feb. 15, 2001

(30) Foreign Application Priority Data

Aug. 4, 1999 (GB) .............................. 9918229

(51) Int. Cl.
| | | |
|---|---|---|
| *B01F 17/00* | (2006.01) | |
| *B01F 3/08* | (2006.01) | |
| *C09K 3/00* | (2006.01) | |
| *C07C 67/38* | (2006.01) | |
| *C07C 51/14* | (2006.01) | |

(52) U.S. Cl. .................... 516/33; 516/31; 560/233; 562/521; 562/522; 568/428

(58) Field of Classification Search ................ 516/31, 516/33; 560/233; 562/521, 522; 568/428, 568/451; 252/1; 518/700

See application file for complete search history.

(56) References Cited

U.S. PATENT DOCUMENTS

| | | | | |
|---|---|---|---|---|
| 2,542,767 | A | * 2/1951 | Gresham et al. ............ 260/483 |
| 4,252,677 | A | * 2/1981 | Smith ......................... 252/430 |
| 4,447,639 | A | 5/1984 | Sofranko et al. | |
| 4,743,358 | A | 5/1988 | Kugler et al. | |
| 4,960,926 | A | * 10/1990 | Drent ........................ 560/233 |
| 5,166,411 | A | 11/1992 | Drent | |
| 6,723,882 | B2 | 4/2004 | Slany et al. | |
| 2003/0191339 | A1 | 10/2003 | Schaefer et al. | |

FOREIGN PATENT DOCUMENTS

| | | |
|---|---|---|
| DE | 197 54 304 | 6/1990 |
| DE | 44 43 705 | 6/1996 |
| DE | 197 45 904 | 4/1999 |
| EP | 0 715 889 A2 | 6/1996 |
| EP | 0 879 642 | 11/1998 |
| WO | WO 96/19434 A1 | 6/1996 |
| WO | WO 98/57918 A1 | 12/1998 |

OTHER PUBLICATIONS

Hidefumi Hirai, "Polymer Effect on Fine Metal Particles and Reactive Metal Complexes" Makromol. Chem. Suppl., vol. 14, p. 55–69 (1985).*
Wang et al., "Carbonylation of Methanol Catalyzed by Polymer–Protected Rhodium Colloid" J. Mol. Catal. A: Chemical vol. 118, pp. 145–151 (1997).*
The Merck Index, 13$^{th}$ ed., MERCK & CO., Whitehouse Station, NJ, pp. 778 and 1374 (2001).*
Wang et al, "Carbonylation of Methanol Catalyzed by Polymer–protected Rhodium Colloid" J. Molecular Catalysis A: Chemical, vol. 118(2), pp. 145–151 (1997). (CAPLUS abstract).*
Harai, H. "Polymer Effect on Fine Metal Particles and Reactive Metal Complexes" Makromolekulare Chemie, Supp. vol. 14, pp. 55–69 (1985). (CAPLUS abstract).*
Wei–Yong Yu et al., "Preparation of Polymer–protected Pt/Co Bimetallic Colloid and its Catalytic Properties in Selective Hydrogenation of Cinnamaldehyde to Cinnamyl Alcohol", Polymers for Advanced Technologies, Aug. 1, 1996, pp. 719–722, vol. 7, No. 8.
Franck Bertoux et al., "Palladium catalyzed hydroxycarbonylation of olefins in biphasic system: Beneficial effect of alkali metal salt and protective–colloid agents on the stability of the catalytic system", Journal of Molecular Catalysis A: Chemical 143 (1999), pp. 23–30.

* cited by examiner

Primary Examiner—Richard L. Raymond
Assistant Examiner—Zachary C. Tucker
(74) Attorney, Agent, or Firm—Marina V. Schneller; Michael A. Sartori; Venable LLP

(57) ABSTRACT

A liquid-phase chemical reaction medium comprises one or more reactants, optionally in the presence of a reaction product(s) and one or more solvents, diluents or other form of liquid carrier, a catalyst system comprising at least a metal or metal compound and optionally further compounds such as ligands or complexing agents; characterized in that the reaction medium further comprises a polymeric dispersant dissolved in said liquid carrier, said polymeric dispersant being capable of stabilizing a colloidal suspension of particles of said metal or metal compound within the liquid carrier. The presence of the polymeric dispersant enables metal formed by catalyst deactivation to be more easily recovered and recycled. Preferably, the polymeric dispersant has sufficiently acidic or basic functionality to stabilize the colloidal suspension of said metal or metal compound.

19 Claims, No Drawings

METAL-COMPOUND CATALYZED PROCESSES

This application was filed under 35 U.S.C. 371, and is the U.S. National Stage of PCT/GB00/02981, filed 2 Aug. 2000.

The present invention relates to chemical processes which rely on the presence of a catalyst comprising a metal compound to enable a reaction to be carried out in an economic fashion. In particular the invention provides improvements which allow the recovery of metals lost from such catalysts, e.g. through catalyst degradation, to be facilitated or increased and for contamination of the reaction system by such metals to be reduced.

One metal-compound catalysed reaction is described in WO 96/19434 which discloses a process for the carbonylation of ethylene and a catalyst system comprising a Group VIII metal, normally palladium, and a phosphine ligand in the presence of a source of anions. This type of catalyst tends to de-activate over the course of a period of continuous operation as the palladium compound is reduced to palladium metal. The regeneration of metal contributes to the economic viability of the process and it is therefore desirable to be able to recover palladium from the reaction process as the catalyst degrades. We have noticed that when a reactor is examined following a period of operation of this type of process, a significant amount of metal has been found adhered to the reactor walls and other surfaces within the reactor. This metal is difficult to recover and may only be recovered during a period of shut-down.

U.S. Pat. No. 4,743,358 describes a method for suppressing the harmful effects of one or more metal contaminants (especially vanadium) on catalysts used in processes that convert higher boiling hydrocarbons to lower boiling fractions, in particular the use of a strontium colloid system in catalytic hydrocarbon conversion processes to react with and trap metal contaminants, thereby resulting in a lower coke make and hydrogen production together with increased activity maintenance of said catalysts. The strontium colloid system is stabilised with a surfactant system comprising one or more of phenates, carboxylates, sulphonates, phosphates and the like.

Metal colloids are used for various reactions, including the preparation of metal catalyst systems. For example, EP-A-715889 describes a shell catalyst containing one or more metals of Group VIII and/or IB on a powder or formed support, these metals being in finely divided form within a shell and a process for their production, by coating the support with aqueous solutions of preformed, mono-or bi-metallic colloids of the catalyst metals, stabilised with strongly hydrophilic surfactants.

DE-A-4443705 describes the use of surfactant-stabilised metallic colloids as water-soluble precursors for supported heterogeneous catalysts. The colloids of Group VIII and Ib metals with particle size 1–10 nm were manufactured in stabilised, water-soluble form by reduction of metal salts in THF, alcohols or water, using hydrides, H, or alkali formates as reducing agents in the presence of strongly hydrophilic surfactants, e.g., betaines, fatty alcohols, polyglycol ethers, fatty esters of ethoxylated carbohydrates, etc. The catalysts are obtained by impregnation of (in)organic supports, e.g., activated C or $La_2O_3$, with aqueous solutions of the colloids.

EP-A-0879642, DE-A-19745904 and DE-A-19754304 describe non-reactive media for the purpose of preparation of heterogenous catalysts. Yu et al (Polymers for Advanced Technologies GB John Willey and Sons, Chichester, Vol 7, no. 81 August 1996, pp 719–722) discloses the manufacture of colloidal particles for catalyst hydrogenation purposes by protection using a polymeric dispersant.

Stabilised metal colloids are also used in electronics and photographic applications, e.g. to achieve deposition of metal particles onto selected surfaces.

Bertoux et al (Journal of Molecular Catalysis A: Chemical 143 (1999) 23–30) describe the use of alkali metal salt and protective colloid agents to maintain catalyst activity and improve the thermal stability of a palladium catalysed hydroxycarbonylation reaction.

We have now found that the use of stabilising compounds in a metal-compound catalysed reaction may be beneficial in improving recovery of metal which has been lost from the catalyst system.

According to a first aspect of the invention a liquid-phase chemical reaction medium comprises one or more reactants, optionally in the presence of a reaction product(s) and one or more solvents, diluents or other form of liquid carrier, a catalyst system comprising at least a metal or metal compound and optionally further compounds such as ligands or complexing agents; characterised in that the reaction medium further comprises a polymeric dispersant dissolved in said liquid carrier, said polymeric dispersant being capable of stabilising a colloidal suspension of particles of said metal or metal compound within the liquid carrier.

The liquid reaction medium may be a solvent for the reaction or may comprise one or more of the reactants or reaction products themselves. The reactants and reaction products in liquid form may be miscible with or dissolved in a solvent or liquid diluent. The catalyst system comprises a metal or metal compound and optionally further compounds such as complexing agents, ligands etc. The catalyst is selected to facilitate the reaction to be carried out and the reaction conditions such as temperature, pressure, reactant concentration etc are normally optimised for the particular reaction. Many examples of such reaction mixtures exist, e.g. the palladium-catalysed carbonylation of ethylene is described in WO 96/19434.

The polymeric dispersant is soluble in the liquid reaction medium, but should not significantly increase the viscosity of the reaction medium in a way which would be detrimental to reaction kinetics or heat transfer. The solubility of the dispersant in the liquid medium under the reaction conditions of temperature and pressure should not be so great as to deter significantly the adsorption of the dispersant molecules onto the metal particles.

The polymeric dispersant is capable of stabilising a colloidal suspension of particles of said metal or metal compound within the liquid reaction medium such that the metal particles formed as a result of catalyst degradation are held in suspension in the liquid reaction medium and are discharged from the reactor along with the liquid for reclamation and optionally for re-use in making further quantities of catalyst. The metal particles are normally of colloidal dimensions, e.g. in the range 5–100 nm average particle size although larger particles may form in some cases. Portions of the polymeric dispersant are adsorbed onto the surface of the metal particles whilst the remainder of the dispersant molecules remain at least partially solvated by the liquid reaction medium and in this way the dispersed metal particles are stabilised against settling on the walls of the reactor or in reactor dead spaces and against forming agglomerates of metal particles which may grow by collision of particles and eventually coagulate. Some agglomeration of particles may occur even in the presence of a suitable dispersant but when the dispersant type and concentration is optimised then such agglomeration should be at a relatively low level and the agglomerates may form only loosely so that they may be broken up and the particles redispersed by agitation.

The polymeric dispersant may include homopolymers or copolymers including polymers such as graft copolymers and star polymers.

Preferably, the polymeric dispersant has sufficiently acidic or basic functionality to substantially stabilise the colloidal suspension of said metal or metal compound.

By substantially stabilise is meant that the precipitation of the metal from the solution phase is substantially avoided.

Particularly preferred dispersants for this purpose include acidic or basic polymers including carboxylic adds, sulphonic acids, amines and amides such as polyacrylates or heterocycle, particularly nitrogen heterocycle, substituted polyvinyl polymers such as polyvinyl pyrrolidone or copolymers of the aforesaid.

Examples of such polymeric dispersants may be selected from polyvinylpyrrolidone, polyacrylamide, polyacrylonitrile, polyethylenimine, polyglycine, polyacrylic acid, polymethacrylic acid, poly(3-hydroxybutyricacid), poly-L-leucine, poly-L-methionine, poly-L-proline, poly-L-serine, poly-L-tyrosine, poly (vinylbenzenesulphonic acid) and poly(vinylsulphonic acid).

Preferably, the polymeric dispersant incorporates acidic or basic moieties either pendant or within the polymer backbone. Preferably, the acidic moieties have a dissociation constant ($pK_a$) of less than 6.0, more preferably, less than 5.0, most preferably less than 4.5. Preferably, the basic moieties have a base dissociation constant ($pK_b$) being of less than 6.0, more preferably less than 5.0 and most preferably less than 4.5, $pK_a$ and $pK_b$ being measured in dilute aqueous solution at 25° C.

Suitable polymeric dispersants, in addition to being soluble in the reaction medium at reaction conditions, contain at least one acidic or basic moiety, either within the polymer backbone or as a pendant group. We have found that polymers incorporating acid and amide moieties such as polyvinylpyrollidone (PVP) and polyacrylates such as polyacrylic acid (PAA) are particularly suitable. The molecular weight of the polymer which is suitable for use in the invention depends upon the nature of the reaction medium and the solubility of the polymer therein. We have found that normally the average molecular weight is less than 100,000. Preferably, the average molecular weight is in the range 1,000–200,000, more preferably, 5,000–100,000, most preferably, 10,000–40,000 e.g. Mw is preferably in the range 10,000–80,000, more preferably 20,000–60,000 when PVP is used and of the order of 1,000–10,000 in the case of PAA.

The effective concentration of the dispersant within the reaction medium should be determined for each reaction/catalyst system which is to be used.

The dispersed metal may be recovered from the liquid stream removed from the reactor e.g. by filtration and then either disposed of or processed for re-use as a catalyst or other applications. In a continuous process the liquid stream may be circulated through an external heat-exchanger and in such cases it may be convenient to locate filters for the palladium particles in these circulation apparatus.

Accordingly we provide according to a second aspect of the present invention a process for the manufacture of a compound comprising the steps of
a) forming in a chemical reactor a liquid phase chemical reaction medium according to the first aspect of the present invention,
b) removing from said reactor a portion of said liquid phase chemical reaction medium,
c) separating said liquid phase chemical reaction medium so as to remove from the liquid as a solid-phase colloidal metal particles formed by decomposition of the catalyst system, which are dispersed in the liquid phase by the polymeric dispersant;
d) optionally returning the liquid portion of said separated reaction medium to the reactor; and
e) optionally processing the recovered metal particles so as to form a further quantity of the catalyst system.

Preferably, the catalyst system is a homogenous catalyst system. Preferably, the metal is a group VIII or group 1B metal, more preferably, a group of VIII metal, most preferably palladium. Preferably, the catalyst system incorporates a phosphine ligand.

We have found the invention to be particularly useful in a process for the manufacture of an alkyl ester by carbonylation of a $C_1$–$C_4$ olefin in the presence of an alkyl alcohol.

Accordingly, there is provided according to a third aspect of the present invention a process for the manufacture of an alkyl ester comprising the steps of:
a) forming in a chemical reactor or a liquid phase chemical reaction medium comprising an alkyl alcohol, an olefin and carbon monoxide in the presence of a catalyst system comprising a metal compound and a ligand compound, (optionally in the presence of the alkyl ester product and/or other solvents, co-catalysts) and a polymeric dispersant which is dissolved in said liquid phase chemical reaction medium, said polymeric dispersant being capable of stabilising a colloidal suspension of particles of said metal or metal compound within the liquid phase chemical reaction medium; at a temperature and pressure under which the olefin is alkoxy-carbonylated to form the alkyl ester product, and subsequent steps b)–e) according to the second aspect of the present invention.

Of particular interest and benefit is the use of the process for the manufacture of methyl propionate and so preferably the liquid-phase reaction medium comprises ethylene and carbon monoxide dissolved in methanol and methyl propionate in the presence of a homogeneous catalyst system comprising a compound of palladium, an organic phosphine ligand and preferably a source of anions; and said polymeric dispersant.

The palladium compound may be selected from tris(dibenzylideneacetone) dipalladium (dba) or other compounds, e.g. palladium acetate.

The catalyst system may include a suitable co-catalyst. Preferably, the chemical reaction comprises the carbonylation of a substrate. Preferably, the reaction is the carbonylation of alkenes, alkynes and/or alcohols. Examples of alkenes include $C_1$–$C_4$ alkenes, preferably, propene. Examples of alcohols include the carbonylation of $C_1$–$C_6$ alcohols, preferably $C_1$–$C_4$, most preferably methanol. Particularly favoured reactions include the hydroformylation of propane to butanal, the carbonylation of methanol to acetic acid, the hydroxy or alkoxy carbonylation of alkenes and alkynes and the methoxycarbonylation of ethene to form methyl propionate.

The chemical reaction may also include the oxidation of alkenes and/or alkynes, for example ethene in the Wacker process.

Preferably, the polymer:metal mass ratio in g/g is between 1:1 and 1000:1, more preferably, between 1:1 and 400:1, most preferably, between 1:1 and 200:1. Preferably, the polymer:metal mass ratio in g/g is up to 1000, more preferably, up to 400, most preferably, up to 200.

The organic phosphine ligand is preferably a bidentate ligand of general formula $(R_3-C)_2P-L^1-X-L^2-P-(C-R_3)_2$, in which each R is independently a pendant, optionally substituted, organic group through which the group is linked to tertiary carbon atom C; $L^1$, $L^2$ are independently a linking group selected from an optionally substituted lower alkylene chain connecting the respective phosphorus atom to the group X and X is a bridging group comprising an optionally substituted aryl moiety to which the phosphorus atoms are linked on available adjacent carbon atoms. Preferably, the pendant groups are optionally substituted lower alkyl, e.g. $C_{1-8}$, and may be branched or linear. The linking groups, $L^1$ and $L^2$, are independently selected from an optionally substituted, particularly lower alkyl, e.g. $C_1$ to $C_4$, substituted, lower alkylene, e.g. $C_1$ to $C_4$ chain. Especially preferred is when both $L^1$ and $L^2$ are methylene. The bridging group X is an aryl moiety, e.g. a phenyl group, which may be optionally substituted, provided that the two phosphorus atoms are linked to adjacent carbon atoms, e.g. at the 1 and 2 positions on the phenyl group. Optional substitution of the aryl moiety may be by other organic groups, e.g. alkyl, particularly $C_{1-8}$, aryl, alkoxy, carbalkoxy, halo, nitro, trihalomethyl and cyano. Furthermore, the aryl moiety may be a fused polycyclic group, e.g. naphthalene, biphenylene or indene. Examples of preferred bidentate ligands include bis(di-tert-butyl phosphino)-o-xylene (also known as 1,2bis(di-tert-butylphosphinomethyl)benzene), bis(di-t-neopentyl phosphino)-o-xylene and bis 1,2(di-tert-butyl phosphino) naphthalene.

The invention will be further described in the following experimental Examples.

EXAMPLES 1–6

Screening experiments to determine the effectiveness of polymeric dispersants to stabilise palladium particles were carried out as described below. The required weights of palladium acetate (0.001 g) and PVP of Mw=25,000 were weighed out into glass sample bottles and 20 ml of methanol was added to each one. The Pd concentration was $2.22 \times 10^{-3}$ moles/liter and the ratio (calculated as gram/gram) of Pd to PVP was varied. The sample bottles were then capped and constantly stirred for 24 hours at ambient temperature and then left to settle. The methanol has the effect of reducing $Pd^{2+}$ to metallic Pd as would occur in a reaction vessel using the $Pd^{2+}$ catalyst in a reducing reaction medium such as methanol. The glass bottles were then visually inspected for palladium particles and for any evidence of adherence of palladium to the walls of the vessel, normally appearing as a mirror. Samples of the particulate matter formed in some of the experiments were analysed by transmission electron microscopy (TEM).

TEM

The samples were diluted with methanol. A drop of each solution was placed onto a TEM grid incorporating a carbon support film. The specimens were then allowed to dry at room temperature prior to examination in a Philips CM12 TEM instrument.

The results, shown in Table 1, show that in the presence of PVP at Pd:PVP ratios above 1:1.97 the palladium produced by the reduction of palladium acetate was dispersed in the methanol and there was no precipitation of the metal or deposition on the walls of the glass vials visible in the samples.

TABLE 1

| Example | Pd:PVP (g/g) | Observations. | TEM observations |
|---|---|---|---|
| 1 | 1:84.9 | Black solution, no precipitate or mirror. | Not analysed |
| 2 | 1:10.5 | Black solution, v. slight precipitate or mirror. | very few agglomerates were noted and the primary particle size had fallen to ~5 nm |
| 3 | 1:1.97 | Black solution, no precipitate or mirror. | no agglomerates with size of greater than 100 nm were observed and the primary particle size was ~10 nm. |
| 4 | 1:0.42 | Black solution, black precipitate. Mirror. | Not analysed |
| 5 | 1:0.21 | Black solution, black precipitate and mirror. | a number of mm sized particles were noted and a number of agglomerates of between 100 nm–500 nm in size were observed. However, these were found to consist of primary particles of ~20 nm in size. |
| 6 (comp) | 1:0 | Weak yellow/brown solution, black precipitate and mirror. | clumps up to 1 mm of particles about 500 nm diameter |

EXAMPLES 7–11

The experimental technique described for Examples 1–6 was repeated using PVP together with an $L_2Pd(dba)$ catalyst. $L_2Pd(dba)$ is a catalyst system prepared by mixing a bidentate phosphine ligand (1,2bis(di-t-butylphosphinomethyl) benzene) with tris(dibenzylideneacetone)dipalladium known as dba. The results are shown in Table 2.

TABLE 2

| Example | Pd:PVP (g/g) | Observations. |
|---|---|---|
| 7 | 1:522 | Black solution, black precipitate, no mirror. |
| 8 | 1:104 | Pale yellow solution, black precipitate, no mirror. |
| 9 | 1:10.4 | Pale yellow solution, black precipitate and slight mirror |
| 10 | 1:10.4 | Pale yellow solution, black precipitate and mirror |
| 11 | 1:0 | Pale yellow solution, black precipitate and mirror |

EXAMPLES 12–16

The experimental technique described for Examples 1–6 was repeated using polyacrylic acid (PAA) having a molecular weight of 2,000 as a dispersant. The results are shown in Table 3.

The results show that even small amounts of PAA were effective in dispersing the metal particles formed by the reduction of $Pd(OAc)_2$ however it appeared that at the higher concentrations of PAA in Examples 12 & 13, the reduction of palladium ions to metallic palladium did not occur in that no metal was visible in the solution.

TABLE 3

| Example | Pd:PAA | Observations. | TEM observations |
|---|---|---|---|
| 12 | 1:69.9 | Yellow solution, no precipitate, no mirror. | |
| 13 | 1:6.9 | Yellow solution, no precipitate, no mirror. | |
| 14 | 1:1.42 | Black solution, no precipitate, no mirror. | colloidal suspension of 10 nm–20 nm particles which were identical to those formed at 0.2:1 PAA/Pd ratio but which showed no tendency to coalesce to form larger agglomerates |
| 15 | 1:0.28 | Black solution, no precipitate, no mirror. | |
| 16 | 1:0.14 | Dark yellow solution, black flakes. Slight mirror. | precipitate was formed by very loos agglomeration of large numbers of small (10 nm–20 nm) primary particles which were eith r sph rical or angular in nature |

EXAMPLE 17 (COMPARATIVE)

Tetraoctylammonium bromide was added into a palladium acetate/methanol mixture in gross excess but the presence of the tetraalkyl salt was found to have little impact on palladium particle stability. Large palladium particles were formed and a mirror was observed on the internal surface of the glass vial.

EXAMPLE 18 (COMPARATIVE)

5 ml of propylene carbonate (PC) was added to 15 ml of methanol containing $2.22 \times 10^{-3}$ moles/l of palladium (ex acetate) a stable black coloured solution was eventually formed. There was no evidence of any mirror formation on the walls of the glass vial and no significant precipitate was observed in the base of the solution. TEM analysis of the PC stabilised solution revealed the presence of roughly spherical particles ranging from 25 nm–150 nm in diameter. However, these particles were distinctly different from those formed in the presence of PVP or PAA in that the particles were "lumpy" spheres which appeared to have some, although poorly defined, sub-structure.

EXAMPLE 19

The effect of polymeric dispersants on catalyst performance was demonstrated in the Pd catalysed methoxycarbonylation of ethylene reaction described in WO 96/19434. $L_2Pd(dba)$ catalyst (where $L_2$ is 1,2bis(di-t-butylphosphinomethyl)benzene ($5.03 \times 10^{-5}$ moles, 37 mg) and methanesulfonic acid (68 μL, $1.0 \times 10^{-3}$ moles) were charged to a two-liter Hastelloy B2 autoclave without exposure to air. The required weight of polymeric dispersant was added to the reaction flask coincident with the addition of the catalyst. A reaction solution generally consisting of 30% w/w methyl propionate in methanol made up to a total volume of 300 ml (81 ml of methyl propionate and 219 ml of methanol) was added to the autoclave and the vessel was heated to 80° C. When at temperature, the autoclave was opened up to a reservoir containing a 1:1 mixture of carbon monoxide and ethylene until a pressure increase of 10 bar had been attained. The reaction was run at these conditions for a further period of 240 minutes during which time the pressure within the autoclave was held constant by feeding gas, as required by the rate of reaction, from the feed reservoir. Assuming ideal gas behaviour and 100% selectivity of the reaction for methyl propionate formation, the magnitude of the pressure drop within the gas reservoir allowed the extent of reaction and the turnover number (TON=moles methyl propionate/mole Pd) to be determined as a function of reaction time. This measure of TON was cross checked against that calculated from the weight gain of the solution at the completion of the experiment. The results are shown in Table 4.

TABLE 4

| Dispersant | dispersant:Pd (g/g) | TON @ 75 mins | TON @ 180 mins | TON @ 240 mins |
|---|---|---|---|---|
| None (comp) | — | 16,067.00 | 25,122.00 | 28,750.00 |
| PVP (Mw = 25k) | 46.9:1 | 20,497.00 | 30,622.00 | 34,427.00 |
| PVP (Mw = 55k) | 46.9:1 | 19,000.00 | 29,148.00 | 32,739.00 |
| PVP (Mw = 25k) | 357:1 | 16,089.00 | 25,324.00 | 28,377.00 |
| PAA (Mw = 2k) | 67.7:1 | 17,206.00 | 27,121.00 | — |
| PC (comp) | 1.6 vol % in reaction mixture | 17,695.00 | 27,506.00 | 30,819.00 |

The results show that the presence of PVP at different concentrations and of different molecular weights in the reaction mixture had little effect on the activity of the catalyst as measured by calculating the turnover number. The presence of PC or PAA was also found to have little impact upon catalyst performance.

EXAMPLES 20 & 21 (COMPARATIVE)

The reaction described in Example 19 was run five times in succession in order to estimate the mass balance of Pd in the reactor and recovered from the reactor. The dispersant used was PVP (average molecular weight=25,000) added to each run at a PVP/Pd ratio of 188. The concentration of $L_2Pd(dba)$ was doubled compared to the reactions in Example 19 in order to generate high levels of palladium for the subsequent chemical analysis procedures and as a consequence, in order to restrain the rate of reaction, a low reaction temperature (60° C.) and a high (70 wt %) methyl propionate concentration was used. Before the start of the series of 5 runs the accessible surfaces within the autoclave were cleaned but between each of the individual runs the autoclave was not cleaned. By this means it was hoped to allow measurable levels of palladium deposition to build up on the internal reactor surfaces and on a clean stainless steel coupon which was suspended within the liquid phase of the system. On conclusion of each series of runs the internal surfaces of the reactor were wiped as clean as practicable and the amount of palladium obtained by this operation was determined by ashing the samples, dissolving the ash and analysing by ICP-AAS. The liquid product from each of the individual runs from each series was combined and then evaporated to a manageable volume (~20 ml) and the quantity of palladium within this material was also determined. The results are shown in Table 5. In Comparative Example 21, the five runs were repeated in a cleaned reactor but no PVP was added to the reaction mixture. The total palladium in the system over the five runs was 0.0532 g. It was noted that the liquid product from the reaction with PVP was a rather black/yellow liquid compared with the reaction product from the Example 21 runs which were clear yellow in colour with some black precipitate as expected from this reaction. This indicates that the physical form of the palladium metal is probably different in the presence of PVP, presumably because the PVP keeps the palladium particles suspended in solution and avoids the formation of large agglomerates which precipitate out of solution.

The results show that the addition of PVP to the reaction system has facilitated the recovery of a larger fraction of the palladium than that recovered in the absence of PVP, even though slightly more Pd was recovered from the reactor walls when PVP was present, possibly because in the presence of PVP the deposits on the walls were easier to remove.

TABLE 5

|  | Example 20 with PVP | Example 21 No PVP |
| --- | --- | --- |
| % Pd on Surfaces | 6.1 | 3.7 |
| % Pd in Liquid Phase | 74.5 | 58.6 |
| Total % of added Pd recovered | 80.6 | 62.3 |

Examination of the stainless steel coupons by scanning electron microscopy on removal from the reactor showed that agglomerates of palladium were present on the surface of the coupon taken from the reaction in comparative Example 21 which were not seen on the coupon removed from the reaction in Example 20. Energy dispersive X-ray analysis (EDX) of the parts of the coupons where no agglomerates were visible showed lower levels of trace contamination on the coupon from Example 20 than that from Example 21.

EXAMPLES 22–25

The experiment described in Example 20 was repeated for a series of four consecutive runs using either no dispersant or PVP (at 188 g/g/Pd), PAA (at 33.8 g/g Pd) or PC (at 3.2 volume %). The reaction conditions differed from Example 20 in that, when at temperature, the autoclave was pressurised to 8 bar of ethylene before the 1:1 mixture was allowed to fill the reactor to 10 bar. This gave a reactant gas mixture of 9:1 ethylene:carbon monoxide. The total palladium in the system over the four runs was 0.0426 g. The palladium was recovered from the surfaces of the reactor and from the total solution gathered from four runs and the results are shown in Table 6.

TABLE 6

|  | Example 22 No dispersant | Example 23 PVP | Example 24 PC | Example 25 PAA |
| --- | --- | --- | --- | --- |
| % Pd on Surfaces | 5.5 | 14.5 | 7.5 | 6.7 |
| % Pd in Liquid Phase | 53.3 | 62.3 | 49.8 | 53.3 |
| Total % of added PD recovered | 58.8 | 76.8 | 57.3 | 60.0 |

The results clearly show that PVP is the preferred polymeric dispersant for use in this particular reaction with the catalyst used because the performance of the catalyst is unaffected whilst the recovery of Pd metal from the liquid reaction medium is enhanced. However, when different metal compound catalyst systems are used then alternative polymeric dispersants may perform better.

EXAMPLES 26–30

In these examples the efficiency as a dispersant of polyacrylic acid (PAA) having a molecular weight of 2,000 was tested in a model system consisting of methanol, methyl propionate, methanesulphonic acid and the $L_2Pd(dba)$ catalyst described in Example 19. In these tests 33 mg of the $L_2Pd(dba)$ catalyst and the required mass of PAA were weighed out into a glass vial and 20 mL of a 50/50 w/w mixture of methanol and methyl propionate was added to the vial. The palladium concentration in these solutions was $2.22 \times 10^{-3}$ moles/L. 60 μL of methanesulphonic acid was then added to the vial. All of the additions were carried out under a blanket of nitrogen and the vial was then sealed and stirred for a period of 7 days. After this time the solutions were visually inspected for signs of palladium deposition. The quantity of PAA added to samples was such that the ratio (g/g) of PAA/Pd in the solutions was varied between 0 and 200. The results of these experiments are shown in Table 7.

TABLE 7

| Example | g PAA/g Pd | Observations |
| --- | --- | --- |
| 26 | No PAA | Yellow solution with black precipitate and mirror on vessel walls |
| 27 | 1 | Yellow solution with black precipitate and slight mirror on vessel walls |
| 28 | 10 | Yellow solution with black precipitate and mirror on vessel walls |
| 29 | 100 | Light yellow solution with black precipitate. No mirror on vessel walls. |
| 30 | 200 | Light yellow solutions with no precipitate. No mirror on vessel walls |

These data suggest that in order to maintain palladium in solution when $L_2Pd(dba)$ catalyst is used as the palladium source then a PAA/Pd ratio of greater than 100 is required. These data satisfactorily explain why no beneficial effect of PAA upon palladium recovery was observed in Example 25 (where the PAA/Pd ratio was only 33.8) and contrast with the efficiency of PAA in preventing palladium deposition when palladium acetate is used as the metal source (Examples 12–16) where a PAA/Pd ratio of only 6.9 was required to inhibit palladium deposition.

EXAMPLES 31 AND 32

These examples were carried out in an identical manner to those described in example 22 (no dispersant) and example 25 (PAA addition). However, in these experiments the PAA addition to the system was carried out at a PAA/Pd ratio of 100. The results from these experiments reveal that only 46.8% of the palladium which was added to the system was reclaimed from the solution phase in example 31 (no dispersant) while the solution phase contained 61.9% of the added palladium when PAA was present at a PAA/Pg ratio of 100 (example 32). These data confirm that PAA is an effective stabiliser which allows palladium to be retained within the solution phase when it is applied at a PAA/Pd ratio of 100.

EXAMPLES 33–41

The examples presented above have demonstrated that stabilisers containing acidic or basic functional groups have the potential to restrain the extent of deposition of palladium from the solution phase onto the walls of vessels. It has also been noted that highly polar stabilisers which are cationic in nature (such as tetraoctylammonium bromide) do not appear to confer these benefits. A further series of screening tests was therefore carried out in order to determine whether stabilisers containing functional groups which can be considered as very weak acids or bases (such as alcohols and esters) have the ability to retain palladium within the solution phase.

A series of screening tests was therefore carried out in a similar manner to those described in examples 1–6. That is, the required weight of palladium acetate (0.001 g) was added to 20 mL of a solvent mixture consisting of a 50/50 wt/wt mixture of methanol and methyl propionate. The required weight of the stabiliser was then added to the system such that the stabiliser/Pd ratio (g/g) in each experiment was 100. The sample bottle was then capped and left for a period of 6 days. The glass sample bottles were then visually inspected for palladium particles and for any evidence of adherence of palladium to the walls of the vessel.

| Example | Stabilizer | Pd:Stabilizer (g/g) | Observations |
|---|---|---|---|
| 33 | Hydroxyethylcellulose | 1:100 | Black solution and black precipitates. No mirror. |
| 34 | Cellulose acetate Mol wt = 30,000 | 1:100 | Slight mirror. |
| 35 | Gum Guar | 1:100 | Black precipitate and mirror. |
| 36 | Poly(ethyleneglycol) Mol wt = 8000 | 1:100 | Black precipitates and mirror formed. |
| 37 | Poly(ethyleneoxide) Mol wt = 200,000 | 1:100 | Mirror formed. |
| 38 | Poly(vinylalcohol) Mol wt = 31,000 – 50,000 | 1:100 | Black precipitates and mirror formed. |
| 39 | n-Butylmethacrylate/ Methylmethacrylate/ 15% Methacrylic acid copolymer | 1:100 | Clear yellow/ orange solution. No mirror. |
| 40 | Ethyl acrylate/ Methylmethacrylate/ 20% Methacrylic acid copolymer | 1:100 | Black solution with no precipitate and no mirror. |
| 41 | None | 1:100 | Black precipitate and mirror. |

These examples reveal that none of the weakly acidic or weakly basic stabilisers are wholly effective in preventing precipitation of palladium containing material from the solution phase or in preventing the formation of mirrors on the glass walls of the sample vessels. However, evidence has again been obtained that materials containing acid functional groups (even when these comprise only a fraction of the mass of a co-polymer) are surprisingly effective in maintaining palladium within the solution phase.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extend to any novel one, or any novel combination, of the features disclosed in this specification (including any accompanying claims, abstract and drawings), or to any novel one, or any novel combination, of the steps of any method or process so disclosed.

What is claimed is:

1. A liquid-phase carbonylation reaction medium comprising one or more reactants, including a substrate selected from the group consisting of alkenes and alkynes, a carbonylation agent and a liquid carrier, for carbonylation of the said substrate, optionally comprising a reaction product(s); a catalyst system comprising at least a metal or metal compound and optionally further compounds such as ligands or complexing agents; characterised in that the reaction medium further comprises a polymeric dispersant dissolved in said liquid carrier, the dispersant comprising acidic or basic polymers and a colloidal suspension of particles of said metal or metal compound within the liquid carrier stabilized by the said polymeric dispersant, the polymeric dispersant having sufficient acidic or basic functionality to substantially stabilize a colloidal suspension of said metal or metal compound.

2. A liquid phase carbonylation reaction medium according to claim preceding 1, wherein the acidic or basic functionality is provided by carboxylic acids, sulphonic acids, amines and/or amides.

3. A liquid phase carbonylation reaction medium according to claim 1, wherein the polymeric dispersant is selected from the group consisting of polyvinylpyrrolidone, polyacrylamide, polyacrylonitrile, polyethylenimine, polyglycine, polyacrylic acid, polymethacrylic acid, poly(3-hydroxybutyricacid), poly-L-leucine, poly-L-methionine, poly-L-proline, poly-L-serine, poly-L-tyrosine, poly (vinylbenzenesulphonic acid) and poly(vinylsulphonic acid).

4. A liquid phase carbonylation reaction medium according to claim 1, wherein the polymeric dispersant incorporates acidic or basic moieties either pendant or within the polymer backbone.

5. A liquid phase carbonylation reaction medium according to claim 4 wherein the acidic moieties have a dissociation constant ($pK_a$) of less than 6.0.

6. A liquid phase carbonylation reaction medium according to claim 4, wherein the basic moieties have a base dissociation constant ($pK_b$) or less than 6.0.

7. A liquid phase carbonylation reaction medium as claimed in claim 1 wherein said polymeric dispersant is selected from the group comprising polyvinylpyrollidone (PVP) and polyacrylates.

8. A liquid phase chemical reaction medium as claimed in claim 1 comprising methanol, ethylene, methyl propionate and carbon monoxide in addition to a catalyst system comprising a palladium compound.

9. A process for the carbonylation of a substrate comprising the steps of
   a. forming in a chemical reactor a liquid phase carbonylation reaction medium according to claim 1, b. removing from said reactor a portion of said liquid phase carbonylation reaction medium, c. separating said portion of liquid phase carbonylation reaction medium so as to remove from the liquid as a solid-phase colloidal metal particles formed by decomposition of the catalyst system, which are dispersed in the liquid phase by the polymeric dispersant;

d. optionally returning the liquid portion of said separated reaction medium to the reactor; and e. optionally processing the recovered metal particles so as to form a further quantity of the catalyst system.

10. A process according to claim 9 wherein the catalyst system is a homogenous catalyst system.

11. A process according to claim 9 wherein the metal is a group VIII or group 1B metal.

12. A process according to claim 9, wherein the catalyst system incorporates a phosphine ligand.

13. A process for the manufacture of an alkyl ester comprising the steps of:

a) forming in a chemical reactor a liquid phase carbonylation reaction medium comprising an alkyl alcohol, an olefin and carbon monoxide in the presence of a catalyst system comprising a metal compound and a ligand compound, optionally in the presence of the alkyl ester product and/or other solvents, co-catalysts and a polymeric dispersant which is dissolved in said liquid phase chemical reaction medium, said polymeric dispersant comprising acidic or basic polymers, said acidic or basic polymers having sufficient acidic or basic functionality to substantially stabilize a colloidal suspension of said metal compound or a metal derived from the metal compound, a stabilised colloidal suspension of particles of said metal compound or the metal of the metal compound within the liquid phase chemical reaction medium; at a temperature and pressure under which the olefin is alkoxy-carbonylated to form the alkyl ester product, and subsequent steps b)–e) according to claim 9.

14. A process as claimed in claim 9, wherein the liquid-phase reaction medium comprises ethylene and carbon monoxide dissolved in methanol and methyl propionate in the presence of a homogeneous catalyst system comprising a compound of palladium, an organic phosphine ligand and optionally, a source of anions; and said polymeric dispersant.

15. A process for the carbonylation of a substrate selected from the group consisting of alkenes and alkynes, comprising the step of: forming in a chemical reactor a liquid phase carbonylation reaction medium; characterised in that the reaction medium further comprises a polymeric dispersant dissolved in a liquid carrier, the dispersant comprising acidic or basic polymers, the polymeric dispersant having sufficient acidic or basic functionality to substantially stabilize a colloidal suspension of a metal or metal compound, and a colloidal suspension of particles of a said metal or metal compound within the liquid carrier stabilized by the said polymeric dispersant.

16. A process according to claim 15, wherein the acidic or basic functionality is provided by carboxylic acids, sulphonic acids, amines and/or amides.

17. A process according to claim 15, wherein the polymeric dispersants may be selected from polyvinylpyrrolidone, polyacrylamide, polyacrylonitrile, polyethylenimine, polyglycine, polyacrylic acid, polymethacrylic acid, poly(3-hydroxybutyricacid), poly-L-leucine, poly-L-methionine, poly-L-proline, poly-L-serine, poly-L-tyrosine, poly(vinylbenzenesulphonic acid) and/or poly(vinylsulphonic acid).

18. A process according to claim 15 wherein the polymeric dispersant incorporates acidic or basic moieties either pendant or within the polymer backbone.

19. A process according to claim 18, wherein the asic moieties have a base dissociation constant ($pK_b$) iof less than 6.0.

* * * * *